(12) United States Patent
Ohara et al.

(10) Patent No.: US 6,468,221 B2
(45) Date of Patent: Oct. 22, 2002

(54) ULTRASONIC ENDOSCOPE

(75) Inventors: Kenichi Ohara, Gunma (JP);
Toshiyuki Hashiyama, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/987,280

(22) Filed: Nov. 14, 2001

(65) Prior Publication Data

US 2002/0062082 A1 May 23, 2002

(30) Foreign Application Priority Data

| Nov. 21, 2000 | (JP) | ..................................... | 2000-353740 |
| Nov. 21, 2000 | (JP) | ..................................... | 2000-353741 |
| Nov. 21, 2000 | (JP) | ..................................... | 2000-353742 |
| Nov. 21, 2000 | (JP) | ..................................... | 2000-353743 |
| Nov. 21, 2000 | (JP) | ..................................... | 2000-353744 |

(51) Int. Cl.$^7$ .............................................. A61B 8/00
(52) U.S. Cl. ...................... 600/462; 600/459; 600/463; 600/466
(58) Field of Search ................. 600/459, 463, 600/445, 393; 29/25.35; 73/632

(56) References Cited

U.S. PATENT DOCUMENTS

| 5,044,053 | A | * | 9/1991 | Kopel et al. ............... 29/25.35 |
| 5,575,288 | A | * | 11/1996 | Sliwa et al. ................ 600/445 |
| 5,685,311 | A | * | 11/1997 | Hara ........................... 600/393 |
| 5,876,345 | A | * | 3/1999 | Eaton et al. ................ 600/463 |
| 6,228,032 | B1 | * | 5/2001 | Eaton et al. ................ 600/463 |
| 6,336,367 | B1 | * | 1/2002 | Raisanen ..................... 73/632 |

* cited by examiner

*Primary Examiner*—Marvin M. Lateef
*Assistant Examiner*—Ruby Jain
(74) *Attorney, Agent, or Firm*—Greenblum & Bernstein, P.L.C.

(57) ABSTRACT

An ultrasonic endoscope has a bending portion, an ultrasonic probe, and a flexible circuit board. The bending portion, connected to the point of a flexible tube, bends along two predetermined bending-directions perpendicular to each other, by remote control. The ultrasonic probe has a plurality of ultrasonic wave vibrators, which are arranged circumferentially, and send ultrasonic waves radially and receive echoes of the ultrasonic waves. The flexible circuit board, which transmits signals associated with the ultrasonic waves and the echoes, is constructed of a plurality of flexible circuit board strips in the bending portion so as to allow a bending motion. The plurality of flexible circuit board strips is durable for the bending motion of said bending portion.

10 Claims, 16 Drawing Sheets

ULTRASONIC ENDOSCOPE

BACKGROUND OF THE INVENTION

1. Field of the Invention

The present invention relates to an ultrasonic endoscope, which uses ultrasonic waves for the diagnosis of a diseased tissue. Especially, the present invention relates to a construction of the portion of the point in the endoscope.

2. Description of the Related Art

In the ultrasonic endoscope, an ultrasonic probe having ultrasonic wave vibrators is provided at the distal end of the endoscope. The ultrasonic probe sends ultrasonic waves and receives echoes of the sent ultrasonic waves.

For the scanning method, a radial scanning or a linear scanning is used. For example, when diagnosing an organ (body-cavity), into which the ultrasonic endoscope cannot be inserted, the radial scanning is performed. The endoscope is inserted toward an organ adjacent to the observed organ, ultrasonic waves are sent radially from the ultrasonic probe. Conventionally, a mechanical-type radial scanning is applied, where a series of ultrasonic wave vibrators is aligned along an axis of the probe and revolves on the axis to send the ultrasonic waves radially.

However, in the case of the mechanical type radial scanning, a color-image, partially colored by Red (R), G (Green), B(Blue), which is effective for diagnosis of the diseased areas, cannot be displayed on the monitor.

Further, while manipulating the bending portion, various forces act on signal transmitting members for transmitting signals associated with the ultrasonic waves and the echoes. Therefore, a greater durability for the bending motion is required for the signal transmitting members provided in the distal end of the endoscope.

SUMMARY OF THE INVENTION

Therefore, an object of the present invention is to provide an ultrasonic endoscope that is capable of obtaining an observed-image for diagnosis, and further that is durable in its bending motion.

An ultrasonic endoscope according to the present invention is an endoscope for performing electronic radial scanning. A bending portion formed in a tube is connected to the point of a flexible tube, which is inserted in a body, or organ. The flexible tube is normally connected to a manipulator portion of the endoscope, and an operator, such as a doctor, bends the bending portion by manipulating a manipulating knob, which is operatively connected to the bending portion. Namely, the bending portion bends by remote control.

An ultrasonic probe for the electronic radial scanning is operatively connected to the bending portion. For example, a solid point-base portion is connected to the bending portion and the ultrasonic endoscope is attached to the point-base portion.

The ultrasonic probe has a plurality of ultrasonic wave vibrators, which are arranged circumferentially to perform the electronic radial scanning. The plurality of ultrasonic wave vibrators send ultrasonic waves radially around a center axis of the ultrasonic probe and receive echoes of the ultrasonic waves.

According to the present invention, a flexible circuit board is provided in the endoscope. The flexible circuit board transmits signals associated with ultrasonic waves and echoes, so that an ultrasonic-image, representing a section-image in the body, is obtained at the ultrasonic wave diagnosis apparatus. As electronic scanning (not mechanical scanning) is performed, an ultrasonic color-image is obtained as required by simultaneously sending multiple ultrasonic waves, each frequency of which is different, or an ultrasonic pulse-width image is obtained by coloring in accordance with contrast of the echoes. These images cannot be obtained by mechanical radial scanning.

In the bending portion, the flexible circuit board is constructed of a plurality of flexible circuit board strips so as to allow a bending motion, namely, to be capable of withstanding the bending motion. The plurality of flexible circuit board strips extends along a central axis of the bending portion. The signal-transmitting member in the bending portion is composed of a plurality of strip-shaped flexible circuit boards, which prevent snapping while the bending portion is manipulated. The plurality of flexible circuit board strips enables the circumferential arrangement of the ultrasonic wave vibrators, namely, the electronic radial scanning. Note that, the width of each flexible circuit board strips is defined in accordance with a radius of the bending portion.

According to the present invention, the plurality of flexible circuit board strips is durable for the bending motion of the bending portion. Speaking concretely, constructions that prevent the flexible circuit board strips from snapping flexure and strengthen the flexible circuit board strips themselves, are shown. Note that, the snapping flexure represents that the flexible circuit board strips are sharply bent, broken or shaped in sharp-wave, which is like a saw wave.

While the bending portion is manipulated, compressing and extending forces operate along the central axis, against the plurality of flexible circuit board strips. Not to cause the snapping flexure, rather to cause smooth and gently flexure when the compressing and extending forces operate, preferably, flexible protecting members are provided. The flexible protecting members extend along the central axis respectively and coat at least one corresponding flexible circuit board strip among the plurality of flexible circuit board strips, respectively. As the thickness of the section of the bending portion increases relative to the flexible circuit board strips, the bending-resistance increases, so that the flexible circuit board strips flexes loosely and smoothly, in other words, flex gently along the central axis. To tightly coat or cover the flexible circuit board strips, preferably, heat shrinking tubes are used as the flexible protecting members. The heat shrinking tubes tightly coat the plurality of flexible circuit board strips after the heat shrinking process. To obtain more durability, preferably, a plurality of bundles, each of which is composed of at least two flexible circuit board strips, is formed using the plurality of flexible circuit board strips. The plurality of bundles may then be coated by using a flexible protecting member for each bundle.

In order not to cause snapping, preferably, the first printed wiring printed on the plurality of flexible circuit board strips is bolder than the second printed wiring printed on a connecting portion of the flexible circuit board, which is connected to the ultrasonic probe. In general, the number of a signal lines of the second printed wiring is determined by the number and arrangement intervals of the ultrasonic wave vibrators. To obtain high-quality ultrasonic-images, it is necessary to arrange a lot of ultrasonic wave vibrators and to have the thinnest printed wiring possible for the second printed wiring. In the bending portion, the first printed wiring becomes bolder than the second printed wiring, which prevents the plurality of flexible circuit board strips from snapping when the plurality of flexible circuit board strips flex.

The flexible circuit board may be formed from a single rectangular flexible circuit board. In this case, the flexible circuit board is formed by partially cutting a single rectangular flexible circuit board such that a plurality of flexible circuit board strips are formed and then rounding the cut rectangular flexible circuit board so as to form a cylindrical shape. To make the first printed wiring bolder, the length of the cut portion of the rectangular flexible circuit board is longer than the length of the connecting portion.

To cause smooth flexure of the plurality of flexible circuit board strips when the compressing and extending forces operate, preferably, flexible sheets that extend along the central axis are provided. Each of the flexible sheets is tightly piled on a corresponding flexible circuit board strip among the plurality of flexible circuit board strips. As the thickness of the bending portion section increases compared to the flexible circuit board strips, the bending-resistance increases, so that the flexible circuit board strips flex smoothly and gently along the central axis. To tightly coat, or cover the flexible circuit board strips, preferably, heat shrinking tubes for tightly coating the plurality of flexible circuit board strips and the flexible sheets by a heat shrinking, are provided.

To cause smooth flexure of the plurality of flexible circuit board strips when the compressing and extending forces operate, preferably, elastic members that extend along the central axis are provided. Each of the elastic members tightly touches a corresponding flexible circuit board strip among the plurality of flexible circuit board strips. As the elastic members absorb the compressing and extending force, the flexure of the flexible circuit board strips become smooth.

In general, the bending portion is composed of a series of ring-shaped segments, which are jointed to each other by hinges. In order not to pinch the plurality of flexible circuit board strips between the series of ring-shaped segments during a bending motion, preferably, each of the elastic members touches the corresponding flexible circuit board strip such that the corresponding flexible circuit board strip is between its elastic member and the central axis in the section of the bending portion. Namely, the elastic members are arranged closer to the circumference than the plurality of flexible circuit board strips. To tightly coat the plurality of flexible circuit board strips, heat shrinking tubes for tightly coating the elastic members and the plurality of flexible circuit board strips by heat shrinking, may be provided. As for the elastic members, preferably, each of the elastic members is an elastic wire, or a coil spring. In the case of elastic wire having elastic characteristics, for example, each of the elastic members is composed of one of the following; metal twist wires, a single metal wire having elastic characteristics, and super-elasticity alloy steel.

BRIEF DESCRIPTION OF THE DRAWINGS

The present invention will be better understood from the description of the preferred embodiment of the invention set fourth below together with the accompanying drawings, in which.

DESCRIPTION OF THE PREFERRED EMBODIMENTS

Hereinafter, the preferred embodiment of the present invention is described with reference to the attached drawings.

Figure 1:
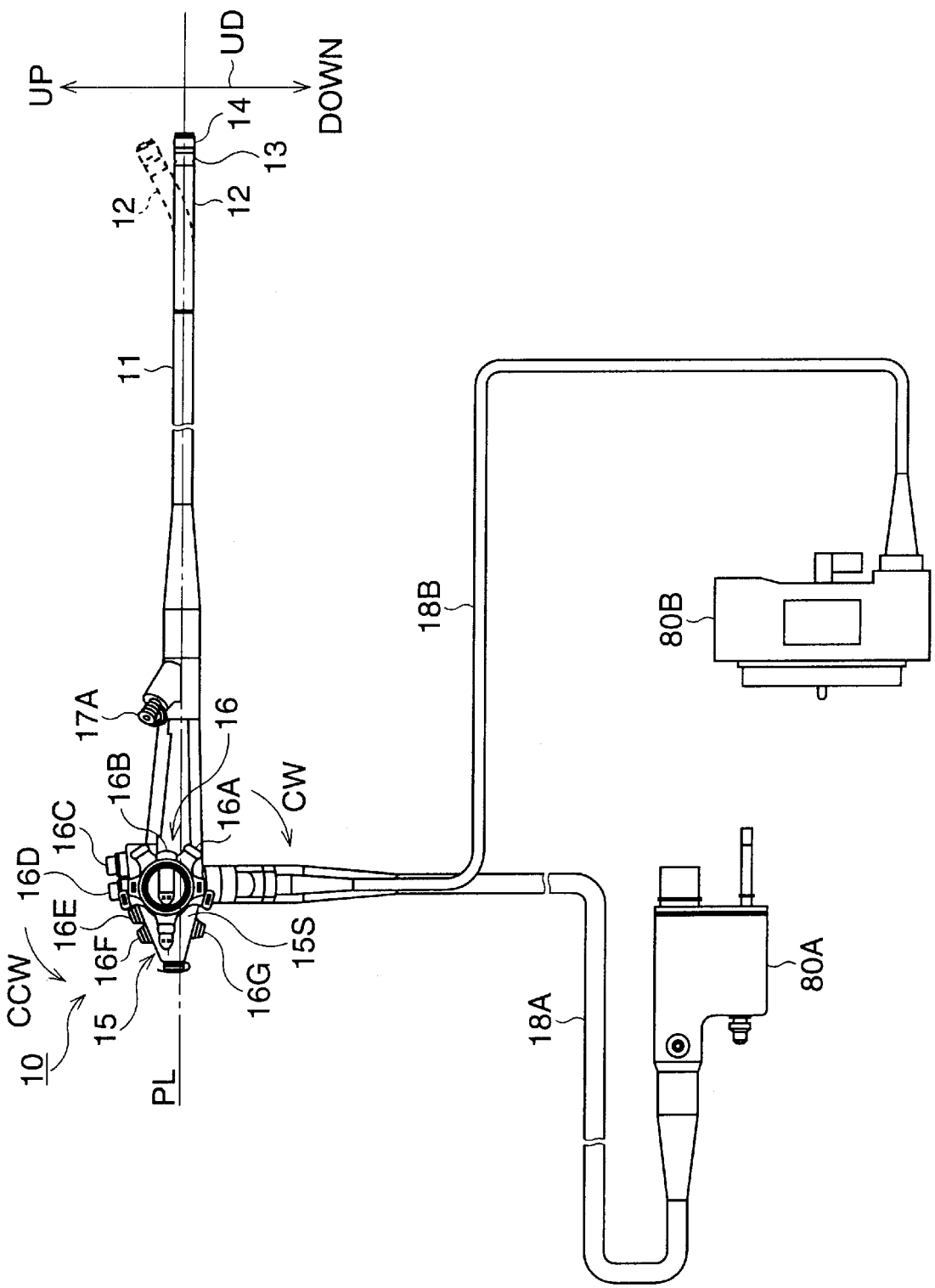
FIG. 1 is a side view of an ultrasonic endoscope of a first embodiment.
Figure 2:
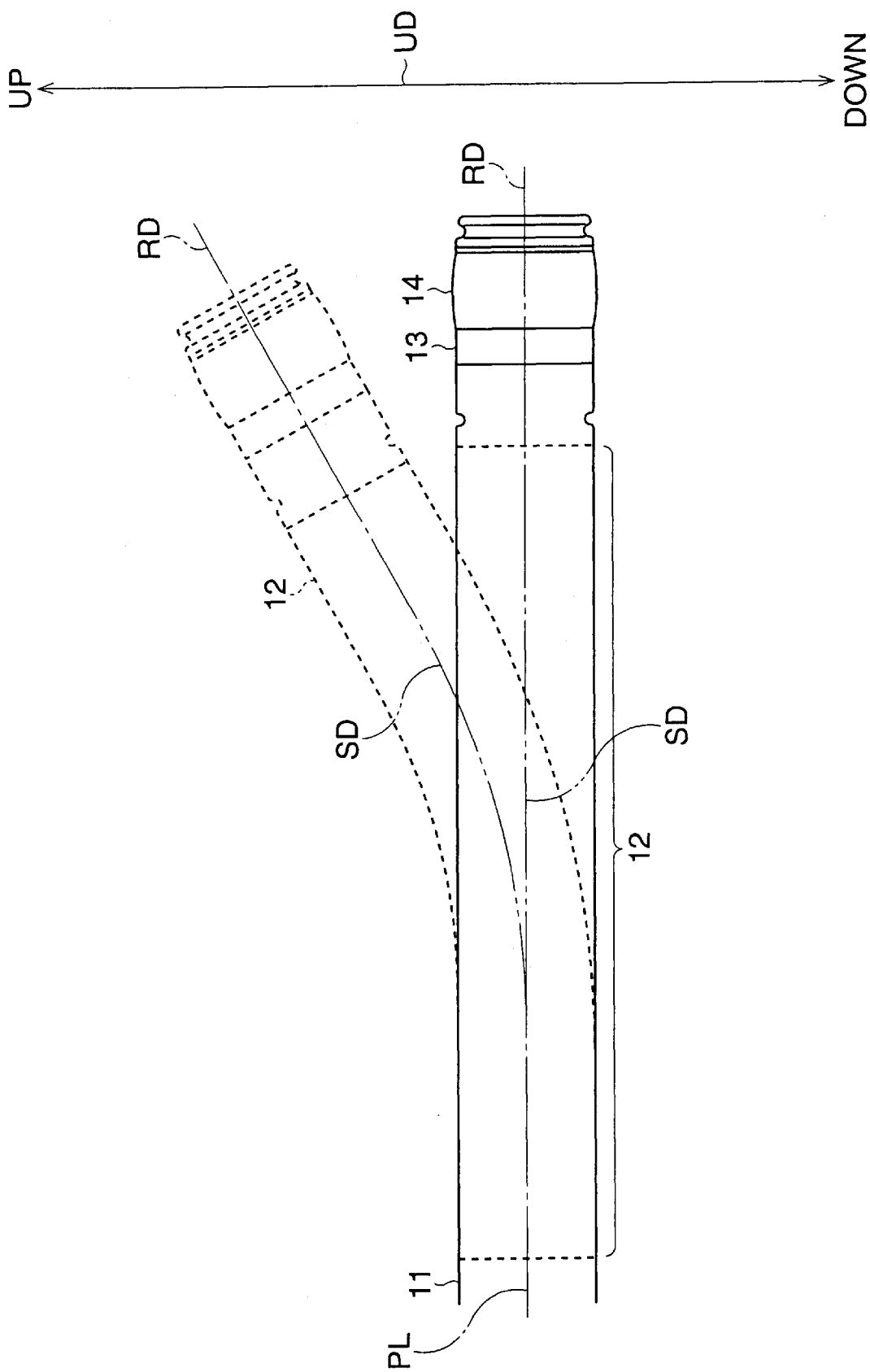
FIG. 2 is a view showing a portion of the point of the ultrasonic endoscope.

FIG. 1 is a side view of an ultrasonic endoscope of the first embodiment. FIG. 2 is a view showing a portion of the point of the ultrasonic endoscope.

An ultrasonic endoscope 10 has a flexible tube 11, manipulator portion 15, first and second connected tubes 18A and 18B, and first and second connecters 80A and 80B. A bending portion 12, a point-base portion 13 and an ultrasonic probe 14 are provided at the distal end of the flexible tube 11, namely, the distal end of the endoscope 10.

The bending portion 12 is connected to the point of the flexible tube 11, the point-base portion 13 is attached to the bending portion 12, and the ultrasonic probe 14 is attached to the point-base portion 13. The first and second connecters 80A and 80B are connected to the first and second connected tubes 18A and 18B respectively, and the first and second connected tubes 18A and 18B are connected to the manipulator portion 15. The flexible tube 11, which is inserted into a given organ (body-cavity), is connected to the manipulator portion 15.

When performing the diagnosis, the first connecter 80A is connected to a video-processor (not shown) having a light source and signal processor circuits, the second connecter 80B is connected to an ultrasonic wave diagnosis apparatus (not shown), and then the flexible tube 11 is inserted into the body-cavity. A first monitor for displaying the observed color image (not shown) is connected to the video-processor and a second monitor for displaying an ultrasonic-image (not shown) is connected to the ultrasonic wave diagnosis apparatus. An operator, such as a doctor, operates a set of manipulating knobs 16, which are composed of an up-down knob 16A and a left-right knob 16B and are provided on the manipulator portion 15, with his right hand. Then, the operator holds the flexible tube 11 in his left hand and inserts the flexible tube 11 toward observed-organ in a patient's body.

A pair of fiber-optic bundles (herein not shown) are provided between the first connector 80A and the ultrasonic probe 14, light radiated from the light source in the video-processor passes through the fiber-optic bundles and is emitted from the distal end of the fiber-optic bundles, namely, the distal end of the ultrasonic endoscope 10. Consequently, an observed-object is illuminated by the light emitted from the fiber-optic bundles.

The ultrasonic endoscope 10 functions as a video-scope. Namely, an objective lens (herein not shown) and an image sensor (not shown), such as a CCD (Charge-Coupled signal cable (herein not shown) connecting the image sensor and the video-processor is provided in the ultrasonic endoscope 10. The light reflected on the object portion passes through the objective lens and reaches the image sensor. Thus, the object image is formed on the image sensor and image signals corresponding to the object image are generated. The image signals are read from the image sensor and fed to the video-processor. In the video-processor, various processes are performed on the image signals, so that video signals, such as an NTSC signal, are generated. The video signals are output to the first monitor so that the object image is displayed on the first monitor.

The bending portion 12 is bent by the operator's remote control, namely, by manipulating the up-down knob 16A and/or the left-right knob 16B. The up-down knob 16A and the left-right knob 16B, provided on the right side surface 15S of the manipulator portion 15, are both rotatable dial type knobs and are connected to the bending portion via wires (herein not shown). The bending portion 12 bends along the two bending directions, namely, the up-down direction shown by "UD" and the left-right direction, by turning the up-down knob 16A and the left-right knob 16B.

When extending the flexible tube 11 so that it is straight and untwisted, the central axis "PL" of the flexible tube 11 becomes a straight-line and the manipulator portion 15 is formed along a central axis "PL" of the flexible tube 11. While the bending portion 12 is in a neutral posture, the bending portion 12 extends along the central axis PL. Therefore, when defining the central axis "SD" of bending portion 12 and the central axis of the point "RD" of the solid point-base portion 13 and the solid ultrasonic probe 14, the central axis SD and the central axis of the point RD coincide with the central axis PL, as shown in FIG. 2.

When the operator turns the up-down knob 16A counterclockwise (shown by "CCW"), the bending portion 12 bends toward the up direction, as shown by the broken line in FIG. 2. Namely, the ultrasonic probe 14 has a given angle to the central axis PL. When the operator turns the up-down knob 16A clockwise (shown by "CW"), the bending portion 12 bends toward the down direction. Similarly, the bending portion 12 bends to the left and right direction by turning the left-right knob 16B counterclockwise or clockwise respectively.

When inserting the flexible tube 11, the operator manipulates the distal end of the endoscope 10 and the flexible tube 11 while watching the color image displayed on the first monitor. Speaking correctly, the operator "shakes" the manipulator portion 15 while holding the manipulating knobs 16 such that the flexible tube 11 turns, or revolves around the central axis PL.

When the ultrasonic probe 14 reaches objective portion, ultrasonic wave pulse signals are output from the ultrasonic wave diagnosis apparatus and are fed to the ultrasonic probe 14 via the second connecter 80B. The ultrasonic probe 14 sends ultrasonic waves on the basis of the ultrasonic wave pulse signals and then receives the echoes of the ultrasonic waves. The echoes are transferred to pulse signals and then the pulse signals are fed to the ultrasonic wave diagnosis apparatus via the second connecter 80B. In the ultrasonic wave diagnosis apparatus, various processes are performed on the input pulse signals corresponding to the echoes, so that an ultrasonic-image, which is a section image along the sending direction of the ultrasonic waves, is displayed on the second monitor.

A forceps tube (herein not shown) is provided between the manipulator portion 15 and the ultrasonic probe 14. A given forceps for treating the diseased portion is inserted from a forceps entrance 17A. Further, a pair of delivery tubes (herein not shown) for supplying water to the point-base portion 13 is provided in the ultrasonic endoscope 10. At the manipulator portion 15, a delivery switch button 16C is provided. When the delivery switch button 16C is operated, the water flows in the delivery tubes and is emitted from the side surface of the point-base portion 13. An absorption switch button 16D, a freeze switch button 16E, a copy switch button 16F, and a recording switch button 16G are provided on the manipulator portion 15. These switches 16C, 16D, 16E, 16F, and 16G are arranged along the up-down direction UD.

Figure 3:
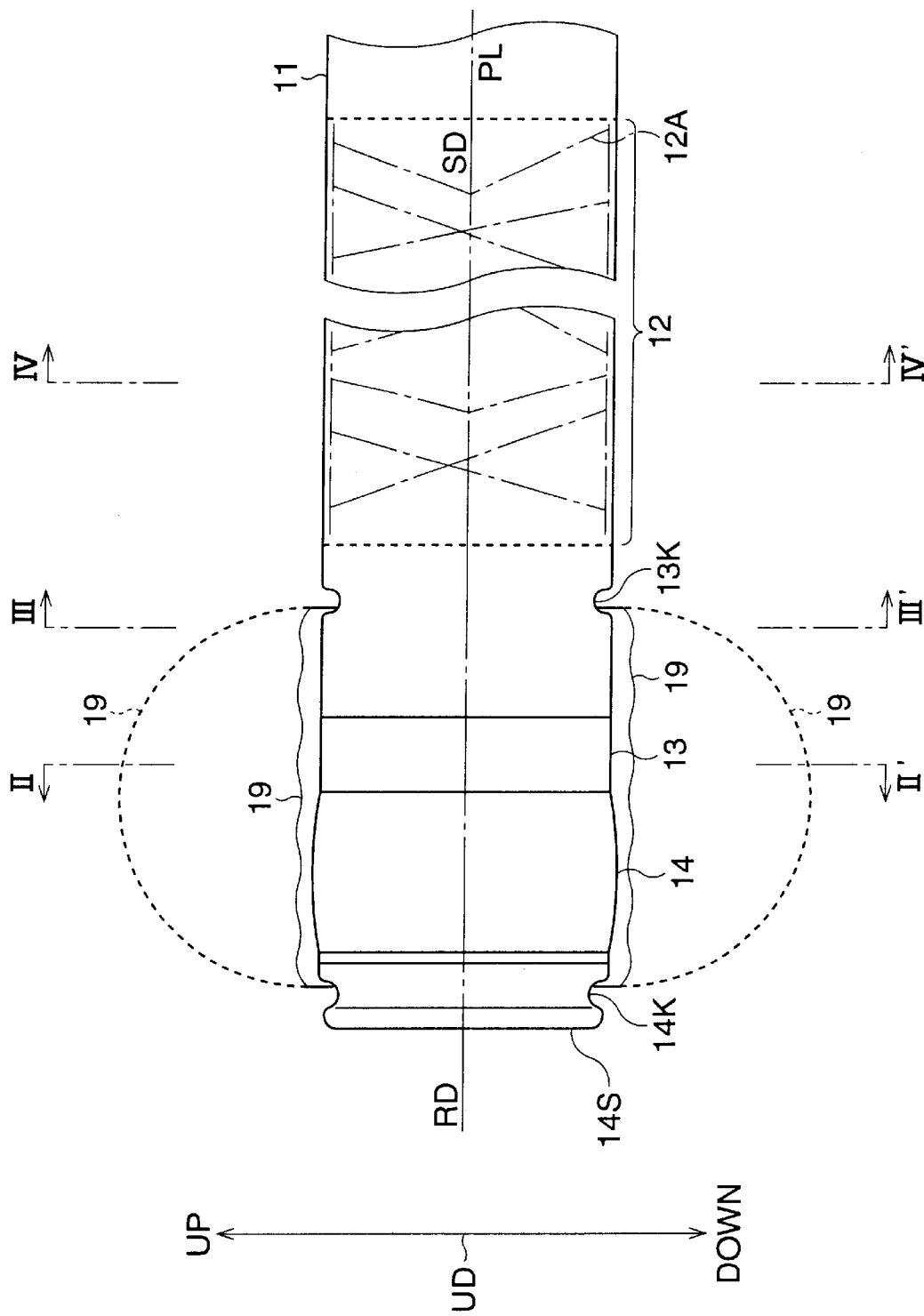
FIG. 3 is a side view showing the point-base portion and the ultrasonic probe, seen from the left side.
Figure 4:
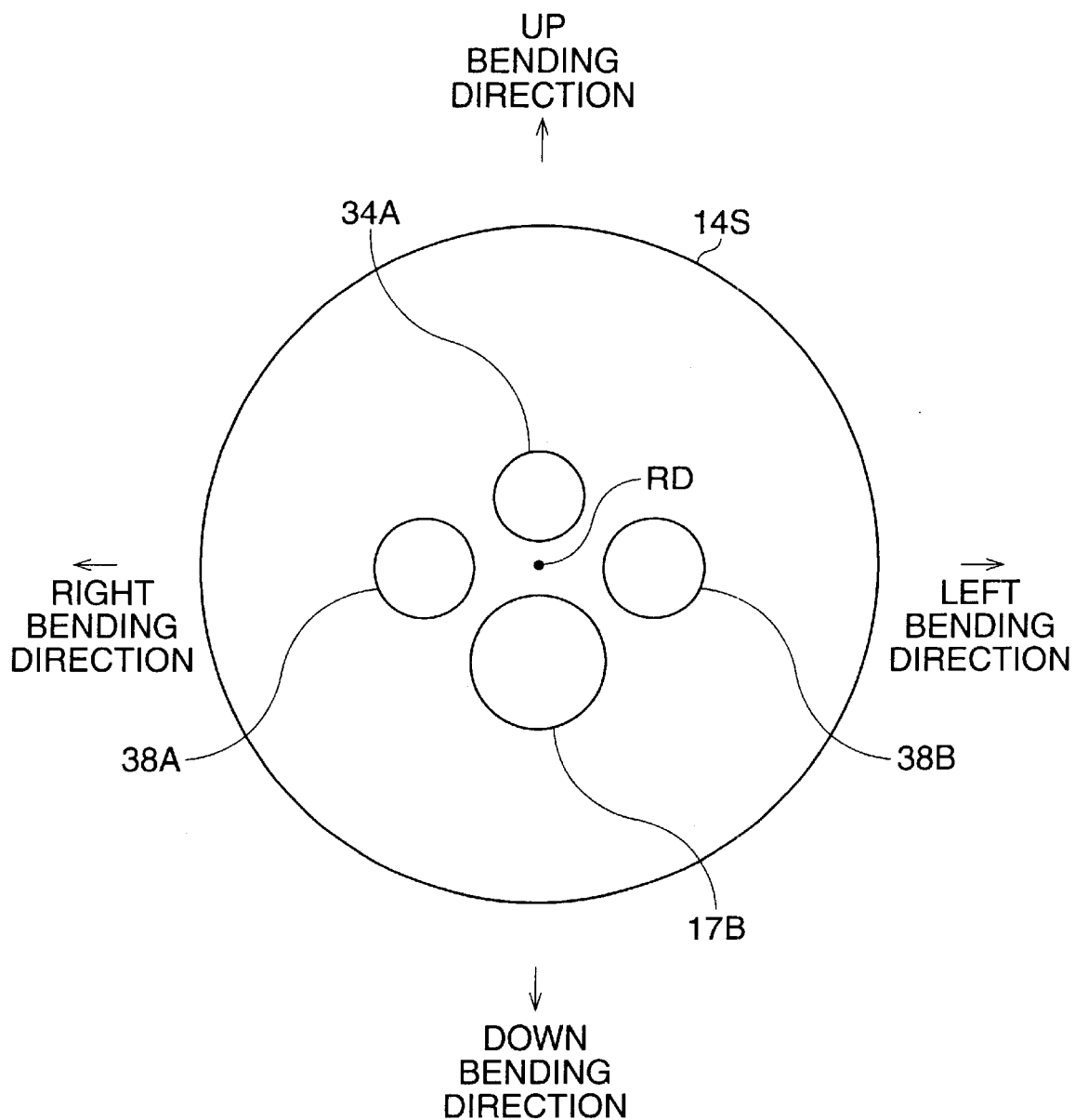
FIG. 4 is a front view of the ultrasonic probe.

FIG. 3 is a side view showing the point-base portion 13 and the ultrasonic probe 14, seen from the left side. FIG. 4 is a front view of the ultrasonic probe 14.

The stiff point-base portion 13 and the ultrasonic probe 14 are covered with a balloon 19 when performing the ultrasonic wave diagnosis. To fix the balloon 19, a first groove 14K is formed around the outer surface of the ultrasonic probe 14 and a second groove 13K is formed around the outer surface of the point-base portion 13. The water, flowing through the delivery tubes, comes out of two outlets (not shown) on the outer surface of the point-base portion 13. To obtain a precise ultrasonic image, the water in a tank (not shown) provided at the video-processor is supplied inside the balloon 19 via the couple of delivery tubes, so that the balloon 19 expands, as shown by the broken line. After the diagnosis, the water in the balloon 19 is absorbed by pushing the absorption switch button 16E and is then fed to an absorbing unit (not shown) via the couple of delivery tubes.

As is well known, the bending portion 12 is formed by continuously linking, or jointing a plurality of ring-shaped segments 12A. The ring-shaped segments 12A are linked by hinge so that the bending portion 12 bends along the up-down direction and the left-right direction.

As shown in FIG. 4, on the front surface 14S of the ultrasonic probe 14, an objective lens 34A is provided, and emitting surfaces 38A and 38B of the fiber-optic bundles and a forceps outlet 17B of the forceps tube are formed. The light, reflected on the subject, passes through the objective lens 34A and reaches the image sensor within the ultrasonic probe 14. The objective lens 34 is provided on the front surface 14S, namely, the point surface of the ultrasonic probe 14 (not side surface). Therefore, the visual field broads along the point central axis RD. As the visual field substantially coincides with the direction of progress of the distal end of the endoscope 10, the operator can insert the flexible tube 11 and manipulate the manipulator portion 15 while looking at the progress of the probe 14.

Figure 5:
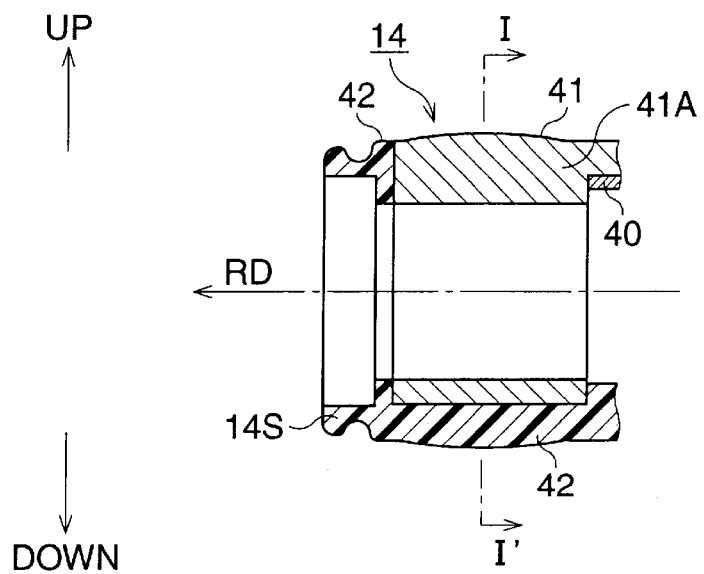
FIG. 5 is a schematic section view of the ultrasonic probe from the side, passing through the center axis of the point and along the up-down direction.
Figure 6:
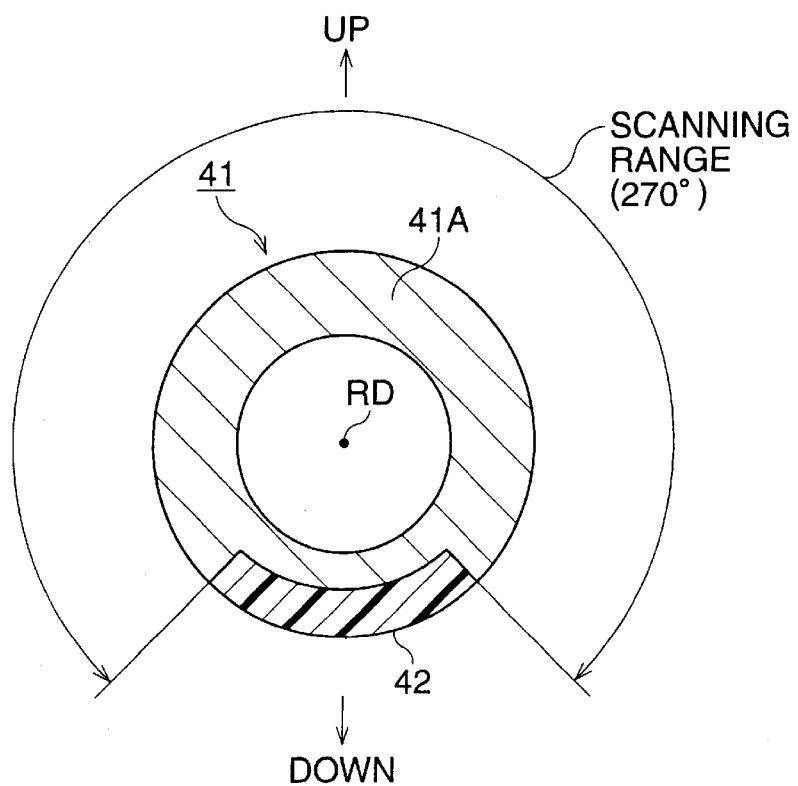
FIG. 6 is a schematic section view of the ultrasonic probe at line I–I' shown in FIG. 5, seen from the front.

FIG. 5 is a schematic section view of the ultrasonic probe 14, passing through the central axis of the point RD and along the up-down direction UD. FIG. 6 is a schematic section view of the ultrasonic probe 14 across the line I–I' shown in FIG. 5, seen from the front surface 14S. Note that, the fiber-optic bundles, forceps tubes, and the image signal cable connected to the image sensor are not shown in FIGS. 5 and 6.

The ultrasonic probe 14 includes an ultrasonic wave sender-receiver 41 and a supporting member 42. The ultrasonic wave sender-receiver 41 is formed along the circumference of the cylindrical ultrasonic probe 14, and the supporting member 42 supports the ultrasonic wave sender-receiver 41. A flexible circuit board 40 for transmitting signals associated with the ultrasonic waves and their echoes is connected to the ultrasonic wave sender-receiver 41. The ultrasonic wave sender-receiver 41 is composed of a plurality of ultrasonic wave vibrators 41A, which are arranged along the circumference of the ultrasonic probe 14 to perform the radial scanning. In this embodiment, each of the plurality of ultrasonic wave vibrators 41A is a piezoelectric element, which transfers electric signals to mechanical vibration and vice versa.

High frequency pulse signals, input to the ultrasonic wave sender-receiver 41 via the flexible circuit board 40, are transformed to ultrasonic waves by the piezoelectric effect. The ultrasonic wave sender-receiver 41 radially sends the ultrasonic waves around the central axis of the point RD, in order. Each of the ultrasonic waves is sent in accordance with a predetermined frequency and timing to perform the electronic radial scanning. In this embodiment, the scanning range is 270 degrees. When the ultrasonic wave sender-receiver 41 receives the echoes in order, the echoes are transformed to given electric signals by the inverse piezoelectric effect. The electric signals are fed to the ultrasonic wave diagnosis apparatus via the flexible circuit board 40.

Figure 7:
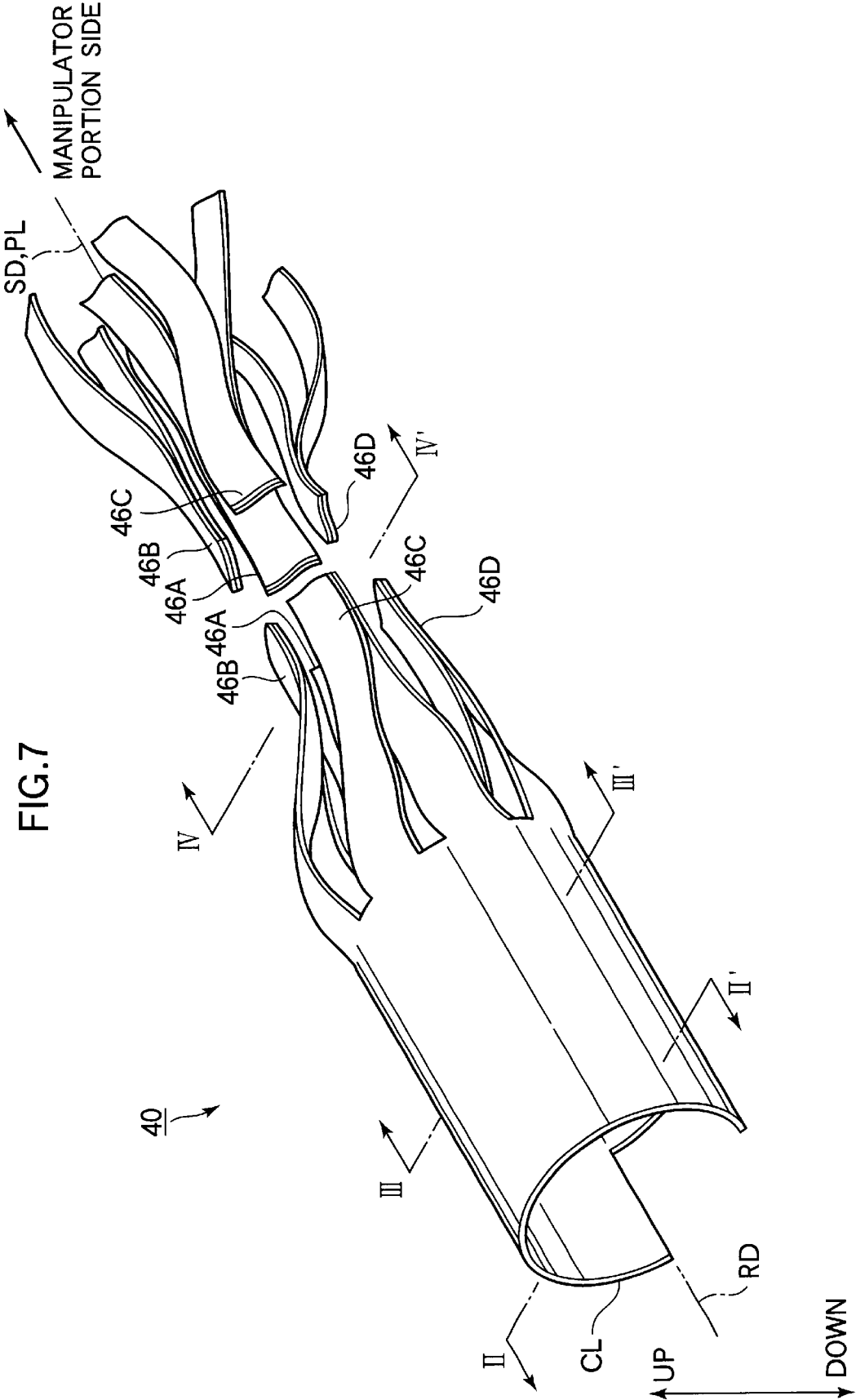
FIG. 7 is a schematic perspective view of the flexible circuit board formed in the endoscope.
Figure 8:
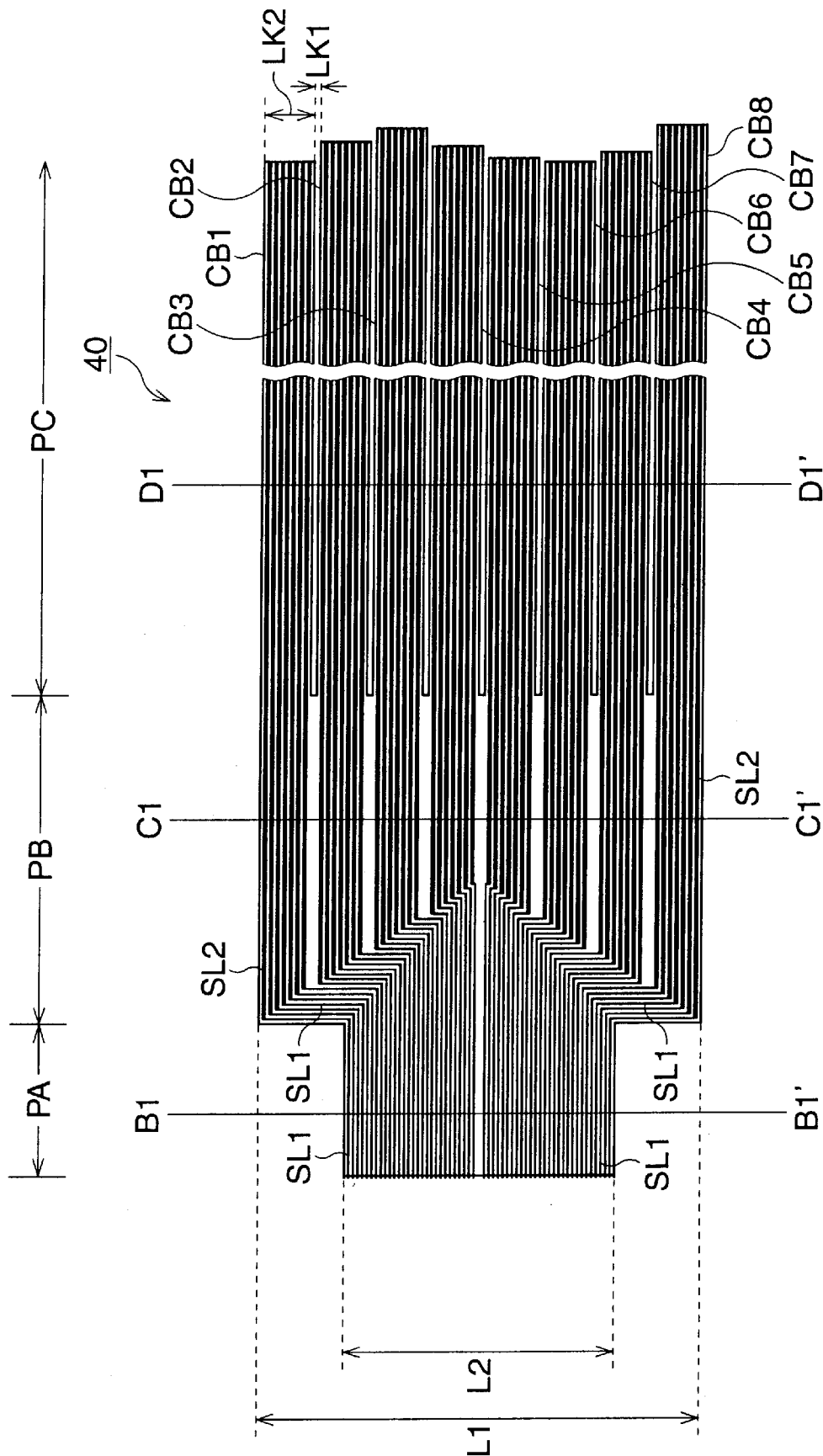
FIG. 8 is a view showing the unfolded flexible circuit board.

FIG. 7 is a schematic perspective view of the flexible circuit board formed in the endoscope 10. FIG. 8 is a view showing the unfolded flexible circuit board.

The flexible circuit board 40 is a flexible and thin substrate, on which circuits are formed. The form of the flexible circuit board 40 can be arbitrarily set, namely, the flexible circuit board 40 can be formed to make any predetermined shape as required. In this embodiment, the flexible circuit board 40 is shaped like a "cone", as shown in FIG. 7. The circumferential line portion "CL" is connected to the arc-shaped ultrasonic wave sender-receiver 41 shown in FIG. 6. In the point-base portion 13, the flexible circuit board 40 is formed in a barrel. In the bending portion 12, the flexible circuit board 40 is constructed of a plurality of flexible circuit board strips. The plurality of flexible circuit board strips are connected to signal lines (herein not shown) extended from the second connector 80B and through the manipulator portion 15. The circuit board strips extend along the central axis SD in the bending portion 12. Note that, in FIGS. 7 and 8, part of the plurality of circuit board strips is omitted, or not shown.

The cone-shaped flexible circuit board 40 is formed by rounding the flat and rectangular flexible circuit board 40' shown in FIG. 8. In FIG. 8, sections PA and PB correspond to the range of the point-base portion 13 and the ultrasonic probe 14. Section PC corresponds to the range of the bending portion 12. The width "L2" at the section PA, namely, the length of the circumference line portion CL, corresponds to the scanning range. The width "L1" at the sections PB and PC, greater than the width "L2", corresponds to a circumferential length of the point-base portion 13 and the bending portion 12. At the section PC, namely, corresponding to the range of the bending portion 12, the rectangular flexible circuit board 40' is divided into the eight strips. Each interval "LK1" between a circuit board strip and adjacent circuit board strip is equal and the width "LK2" of each circuit board strip is equal. Note that, the longitudinal length is different in each circuit board strips. Hereinafter, the eight circuit board strips are designated by "CB1, CB2, ..., and CB8".

As shown in FIG. 8, printed wiring, namely, conduct lines are formed on the rectangular flexible circuit board 40'. The rectangular flexible circuit board 40' is rounded such that the printed wiring is on the inner side of the cone-shape. The number of signal lines in each of the flexible circuit board strips CB1 to CB8 is the same. Note that, printed wiring is not shown in FIG. 7.

Printed wiring SL2, which is printed in the section PC corresponding to the bending portion 12 and part of the section PB, is bolder than the printed wiring SL1, which is printed in the section PA corresponding to the ultrasonic probe 14, and the other part of the section PB. The printed wiring SL2 and the printed wiring SL1 are connected at the section PB. The number of signal lines and boldness of the printed wiring SL1 depends upon the arrangement-number of the ultrasonic wave vibrators 41A and the arrangement-intervals of the ultrasonic wave vibrators 41A. On the other hand, the boldness of the printed wiring SL2 is defined in accordance with the widths "L1", "LK1", and "LK2", so as to prevent the flexible circuit board strips CB1 to CB8 from snapping while bending the bending portion 12.

Figure 9A:
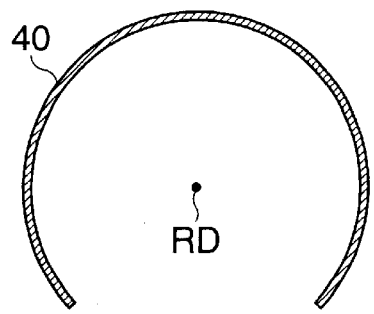
FIGS. 9A to 9C are section view s of the flexible circuit board in the point-base portion and the bending portion.
Figure 9B:
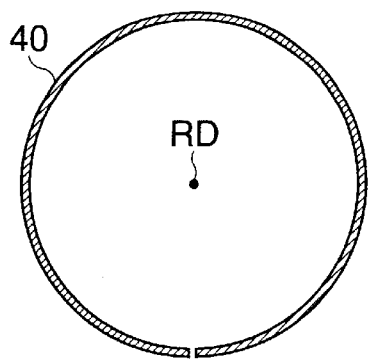
Figure 9C:
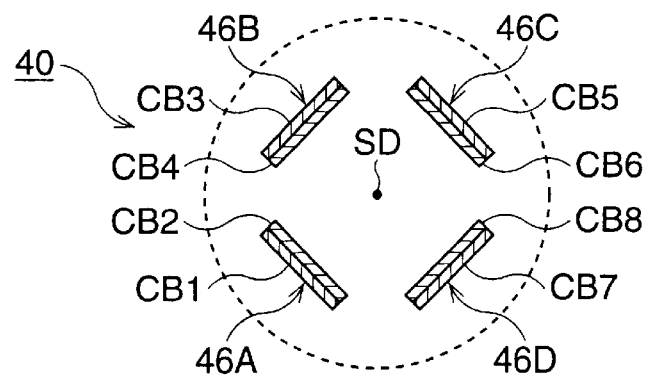

FIGS. 9A to 9C are section views of the flexible circuit board 40 in the point-base portion 13 and the bending portion 12. FIG. 9A is a section view at the line II–II', FIG. 9B is a section view at line III–III', and FIG. 9C is a section view at line IV–IV'. Note that, the lines II–II', III–III', IV–IV' are shown in FIGS. 3 and 7. The section view at the line II–II' is a section view in the point–base portion 13 and near to the ultrasonic probe 14. On the other hand, the section view at line III–III' is a section view in the point-base portion 13 and near to the bending portion 12. A section view at line IV–IV' is a section view in the bending portion 12. Lines B1–B1', C1–C1', D1–D1', shown in FIG. 8, correspond to the lines II–II', III–III', IV–IV', respectively.

As shown in FIG. 9A, the flexible circuit board 40 is formed in an arc, approximately 270 degrees, in accordance with the arc-shaped ultrasonic wave sender-receiver 41, namely, the scanning range. On the other hand, the flexible circuit board 40 is formed in a circle at the line III–III' (See FIG. 9B). Then, as shown in FIG. 7 and FIG. 9C, a circuit board strip and an adjacent circuit board strip among the eight circuit board strips CB1 to CB8, are bundled so that they form four couples or bundles 46A, 46B, 46C, and 46D. The circuit board bundle 46A is composed of the two circuit board strips CB1 and CB2. Similarly, The circuit board bundles 46B, 46C and 46D are composed of the two circuit board strips CB3 and CB4, CB5 and CB6, CB7 and CB8, respectively. At the neighborhood of the flexible tube 11, the four circuit board bundles 46A to 46D are again separated into the eight circuit board strips CB1 to CB8.

Figure 10:
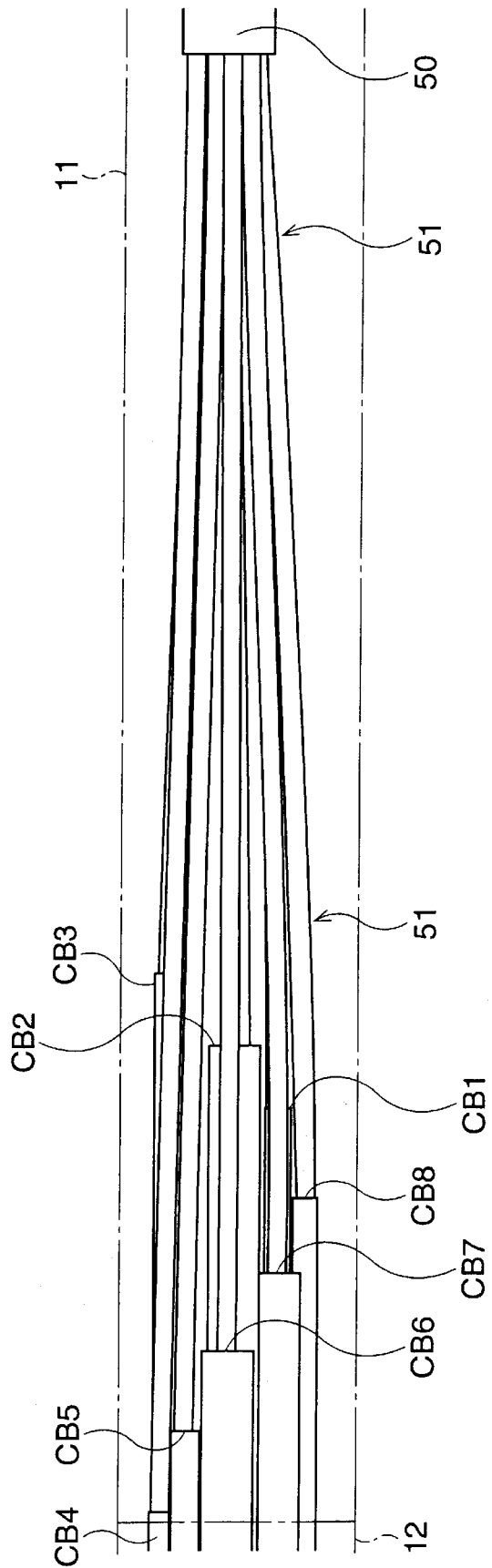
FIG. 10 is a schematic view of the signal lines in the flexible tube.

FIG. 10 is a view showing the signal lines in the flexible tube 11 schematically. The separated eight circuit board strips CB1 to CB8 are connected to eight signal lines 51. The eight signal lines 51 are bundled and formed as an ultrasonic wave single cable 50, which extends between the flexible tube 11 and the second connecter 80B.

Figure 11:
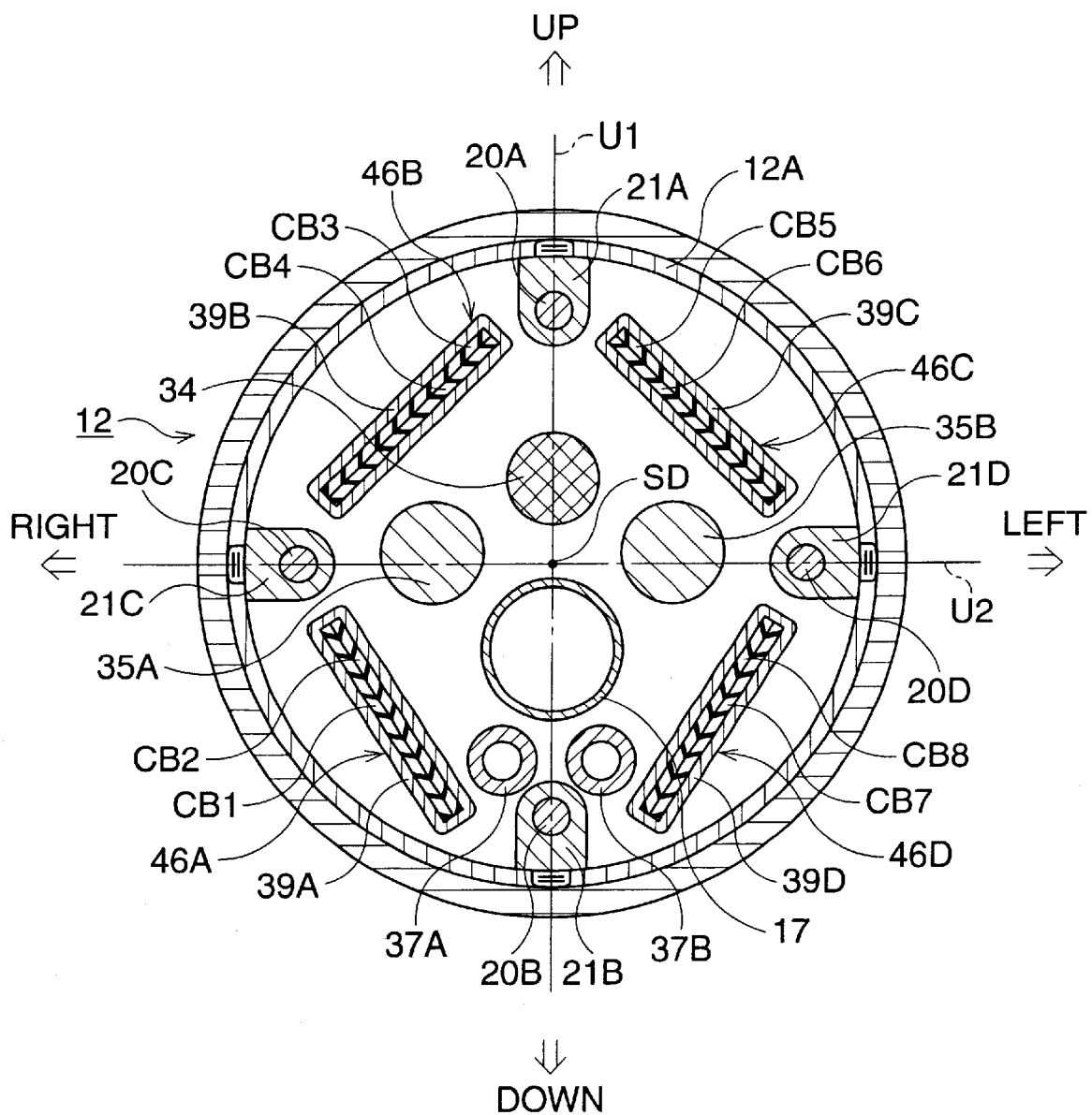
FIG. 11 is a section view of the bending portion, seen from the point side.

FIG. 11 is a section view of the bending portion 12, seen from the point side.

Wire guides 21A, 21B, 21C, and 21D are provided between the manipulator portion 15 and the bending portion 12, and are arranged along the circumference of the flexible tube 11 and the ring-shaped segments 12A of the bending portion 12, at the interval of 90 degrees.

The wire guides 21A and 21B are positioned along the up-down direction UD, and the wire guides 21C and 21D are positioned along the left-right direction. The wires 20A, 20B are installed in the wire guides 21A and 21B, respectively. Similarly, the wires 20C and 20D are installed in the wire guides 21C and 21D, respectively. The bending portion 12 bends toward the up or down direction by moving the wires 20A and 20B operatively connected to the up-down knob 16A, and bends toward the left or right direction by moving the wires 20C and 20D operatively connected to the left-right knob 16B. As shown in FIG. 11, in the bending portion 12, the forceps tube 17, image signal cable 34, the fiber-optic bundles 35A and 35B, and the delivery tubes 37A and 37B are provided.

The fiber-optic bundles 35A and 35B and the delivery tubes 37A and 37B are arranged so as to have symmetry with respect to a central line U1. Note that, the central line U1, defined in the section of the bending portion and crossing the central axis SD of the bending portion 12, corresponds to the up-down direction UD. The image signal cable 34 and the forceps tube 17 are arranged on the up-down central line U1 so as to have symmetry with respect to the central line U1. Note that, a left-right central line U2, defined in the section passing the central axis SD and perpendicular to the up-down central line U1, corresponds to the left-right direction.

As described above, in the bending portion 12, the flexible circuit board 40 is shaped in the four circuit board bundles 46A, 46B, 46C, and 46D. The circuit board bundle 46A is tightly coated by a flexible heat shrinking tube 39A so that the circuit board bundles 46A and the heat shrinking tube 39A are unified. Similarly, the circuit board bundles 46B, 46C, and 46D are tightly coated by flexible heat shrinking tubes 39B, 39C, and 39D, respectively. Each of the heat shrinking tubes 39A to 39D is provided as a protecting member for protecting against the compressing and extending forces, which operate against the flexible circuit board strips CB1 to CB8 along the central axis SD. Each of the heat shrinking tubes 39A to 39D is composed of synthetic resin, such as polyester resin, polyethylene resin, fluorine resin, or silicone plastic. Firstly, the circuit board bundles 46A to 46B are loosely covered with the heat shrinking tubes 39A to 39D respectively, and then are heated. Consequently, the heat shrinking tubes 39A to 39D tightly cover the circuit board bundles 46A to 46D respectively by the heat shrinking process. When the compressing force operates by moving the bending portion 12, the circuit board strips CB1 to CB8 bend smoothly and gently.

The circuit board bundles 46A, 46B, 46C, and 46D are arranged around the image signal cable 34, the fiber-optic bundles 35A and 35B, the delivery tubes 37A and 37B, and the forceps tubes 17, and are arranged generally along straight lines connecting the four wires 20A, 20B, 20C, and 20D. Therefore, the four circuit board bundles 46A, 46B, 46C, and 46D are at an angle of an generally 45 degrees to the up-down central line U1, and are not arranged on the central line U1. Further, the four circuit board bundles 46A, 46B, 46C, 46D are arranged so as to have symmetry with respect to the up-down central line U1 and the left-right central line U2.

In the bending portion 12, powder lubricants, such as a molybdenum disulfide, are filled. Therefore, the positions of the four circuit board bundles 46A, 46B, 46C, 46D, the image signal cable 34, the fiber-optic bundles 35A and 35B, the delivery tubes 37A and 37B and the forceps tube 17 do not substantially change while moving the bending portion 12.

In this way, in this embodiment, the ultrasonic wave sender-receiver 41 is formed along the circumference of the ultrasonic probe 14, namely, the plurality of ultrasonic wave vibratos are arranged along the circumference. The ultrasonic waves are sent radially around the central axis RD for performing the electronic radial scanning. Then, the flexible circuit board 40 is provided for transmitting the signals associated with the ultrasonic waves and the echoes. In the bending portion 12, the flexible circuit board 40 is constructed of the eight circuit board strips CB1 to CB8, and unified in the four circuit board bundles 46A, 46B, 46C, and 46D.

Further, in this embodiment, the printed wiring SL2 is bolder than the printed wiring SL1 to prevent the flexible circuit board strips CB1 to CB8 from snapping, and the circuit board bundles 46A to 46D are tightly coated by the heat shrinking tubes 39A to 39D, respectively. As the circuit board bundles 46A to 46D are tightly coated by the heat shrinking tubes 39A to 39D, the thickness of each of the circuit board bundles 46A to 46D in the section, in other words, the section area of each bundle on the section increases compared to the circuit board strips CB1 to CB8. Thus, when the circuit board bundles 46A to 46D bend because of the compressing force, the circuit board bundles 46A to 46D do not sharply flex and break along the central axis SD, rather the circuit board bundles 46A to 46D flex smoothly. Consequently, snapping of the printed wiring on the flexible circuit board 40 does not occur while moving the bending portion 12.

Figure 12:
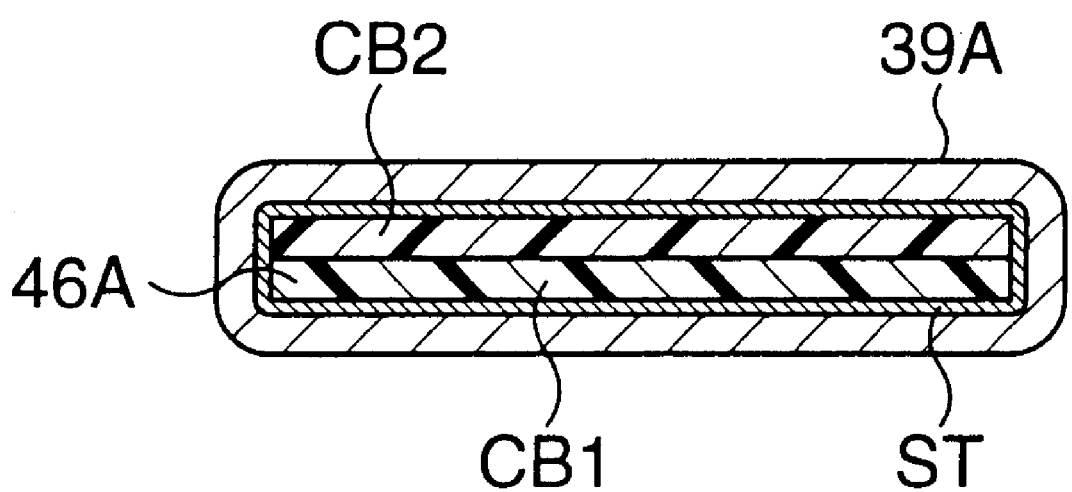
FIG. 12 is a section view of one circuit board bundle, which is covered with a silicon elastic tube.

To tightly cover the circuit board bundles 46A to 46D in a layer, the flexible circuit board strips CB1 to CB8 may be covered with elastic tubes, such as silicone elastic tubes, before performing the heat shrinking. FIG. 12 is view showing a section of a flexible circuit board strip. Before the heat shrinking, the flexible circuit board strips CB1 and CB2 are covered with a silicone elastic tube ST to bundle two circuit board strips CB1 and CB2 tightly. Then, the circuit board bundle 46A, covered with the silicone elastic tube ST, is coated by the heat shrinking tube 39A. Similarly, the circuit board bundles 46B, 46C, and 46D are covered with silicone elastic tubes (not shown).

Figure 13:
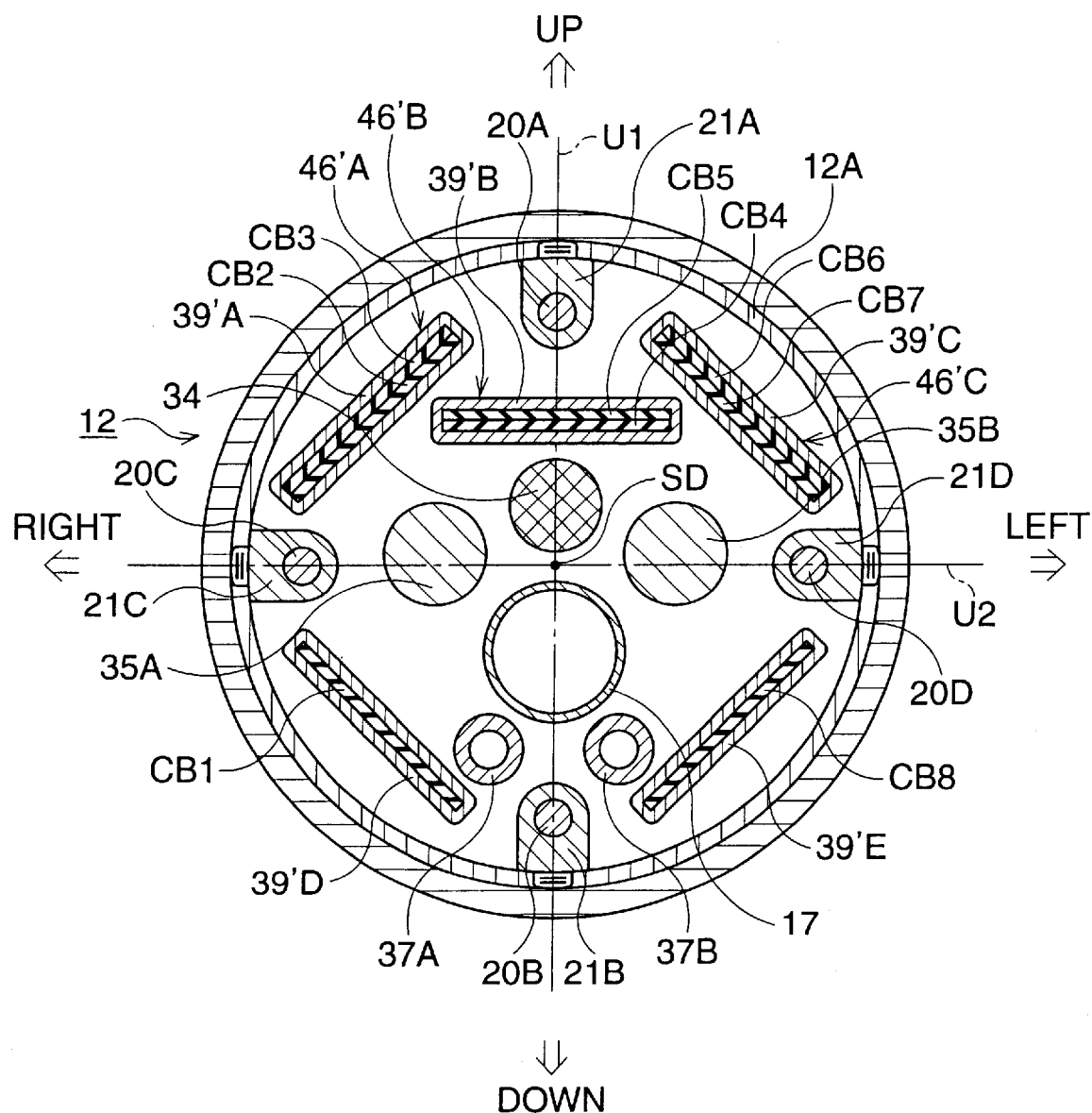
FIG. 13 is a section view of a bending portion of a second embodiment.

With reference to FIG. 13, an ultrasonic endoscope of a second embodiment is explained. The second embodiment is different from the first embodiment with respect to an arrangement of the flexible circuit board strips.

FIG. 13 is a section view of a bending portion of the second embodiment.

In the second embodiment, the eight flexible circuit board strips CB1 to CB8 are separated into three circuit board bundles, each of which has two circuit board strips, and two independent circuit board strips. The circuit board bundle 46'A is composed of the circuit board strips CB2 and CB3, the circuit board bundle 46'B is composed of the circuit board strips CB4 and CB5, and the couples of circuit board bundle 40'C are composed of the circuit board strips CB6 and CB7. The two circuit board strips CB1 and CB8 independently extend along the central axis SD. The three circuit board bundles 46'A, 46'B, and 46'C are covered with heat shrinking tubes 39'A, 39'B, 39'C respectively. The two circuit board strips CB1 and CB8 are covered with heat shrinking tubes 39'D and 39'E, respectively. The three circuit board bundles 46'A, 46'B, and 46'C, and the two circuit board strips CB1 and CB8, are arranged such that the bending-resistance occurs symmetrically with respect to the up-down central line U1.

In this way, in the bending portion 12, the flexible circuit board strips CB1 to CB8 may be arbitrarily bundled or independent without bundling. In this case, the heat shrinking tubes are prepared in accordance with the number of bundles and the number of independent flexible circuit board strips.

In the first and second embodiments, the eight circuit board strips CB1 to CB8 are formed by partially cutting the single rectangular flexible circuit board 40'. However, the flexible circuit board 40' may be partially cut such that the number of circuit board strips is a number other than eight (for example, twelve). Further, in place of utilizing a partially-cut flexible circuit board 40', the flexible circuit board 40 may be composed of a plurality of flexible circuit board strips. In this case, each of the flexible circuit board strips is connected to the ultrasonic wave sender-receiver 41. The thickness and width of each circuit board strips may be defined in accordance with the radius of the bending portion.

The scanning range may be defined for ranges other than 270 degrees. In this case, the widths "L1" and "L2", and the boldness of the printed wiring SL1 and the printed wiring SL2 are defined in accordance with the determined scanning range. In place of the heat shrinking tubes 39A to 39D, other flexible members may be used for protecting the flexible circuit board strips CB1 to CB8 from snapping.

In the first and second embodiments, the ultrasonic endoscope 10 has two constructions in which the printed wiring on the flexible circuit board strips is bold and the flexible circuit board strips are coated by the flexible heat shrinking tubes, however, the ultrasonic endoscope may have only one of the two constructions.

Figure 14:
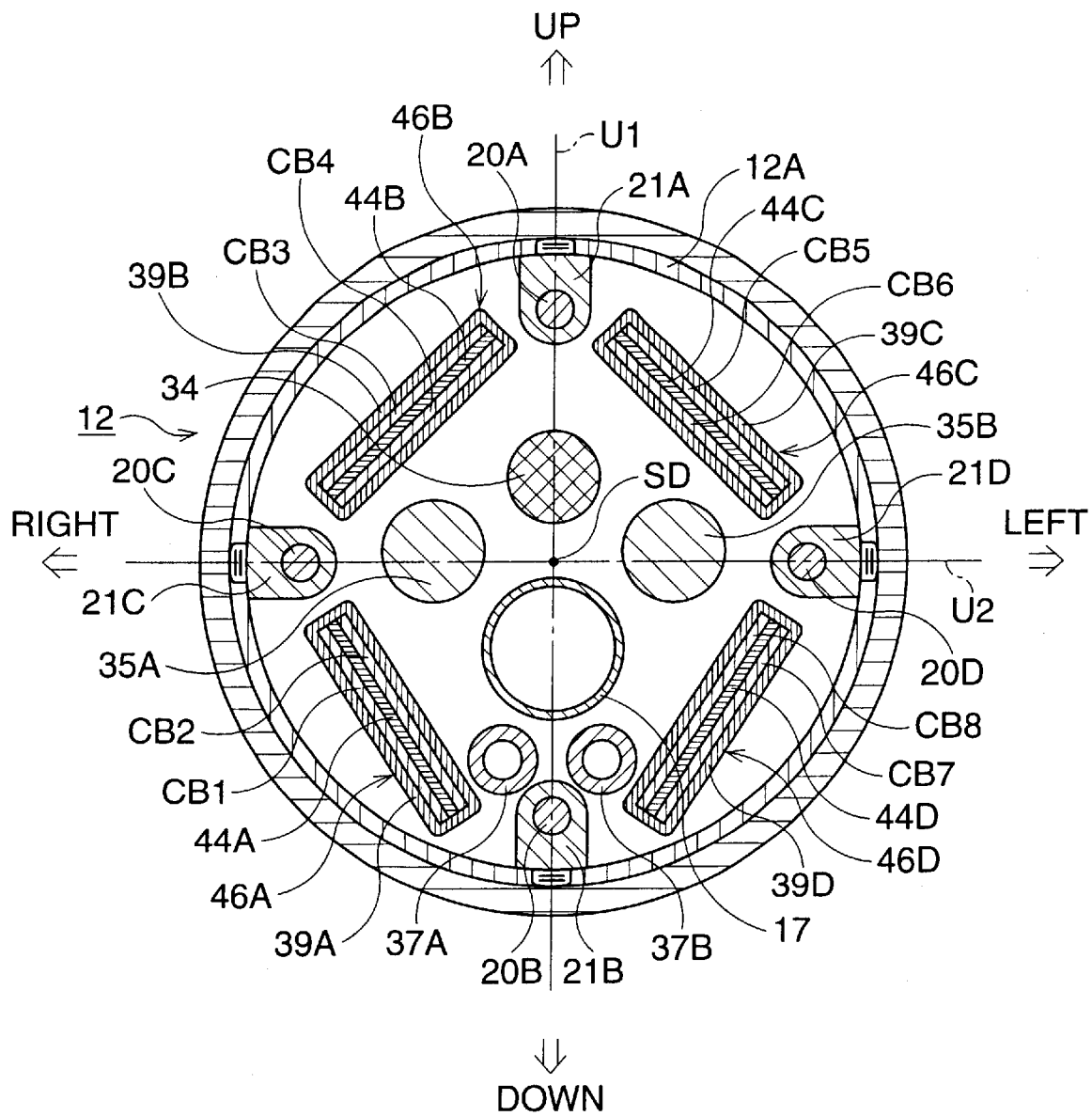
FIG. 14 is a section view of a bending portion of a third embodiment.

With reference to FIGS. 14 and 15, a third embodiment will be explained. FIG. 14 is a different from the first embodiment in that flexible and electric non-conductance sheets are provided.

FIG. 14 is a section view of a bending portion of the third embodiment.

Flexible and electric non-conductance sheets 44A to 44D extend along the central axis SD, similarly to the flexible circuit board strips CB1 to CB8, and the width of each of the flexible sheets 44A to 44D is substantially the same as the width "LK2" of the flexible circuit board strips C1 to C8. The flexible sheet 44A is put between the flexible circuit board strips CB1 and CB2 such that the flexible sheet 44A and the flexible circuit board strips CB1 and CB2 are piled up, or arranged in layer. The flexible sheet 44A and the flexible circuit board strips CB1 and CB2 are tightly coated by the heat shrinking tube 39A. Similarly, the flexible sheet 44B is put between the flexible board strips CB3 and CB4, the flexible sheet 44C is put between the flexible board strips CB5 and CB6, and the flexible sheet 44D is put between the flexible board strips CB7 and CB8. Each of the flexible sheets 44A to 44D is composed of polyester resin, polyethylene resin, or fluorine resin.

In this way, the thickness of each of the circuit board bundles 46A to 46D on the section increases by the flexible sheets 44A to 44D. Thus, when the circuit board bundles 46A to 46D bend because of the compressing force, the circuit board bundles 46A to 46D do not sharply flex and break along the central axis SD.

Figure 15A:
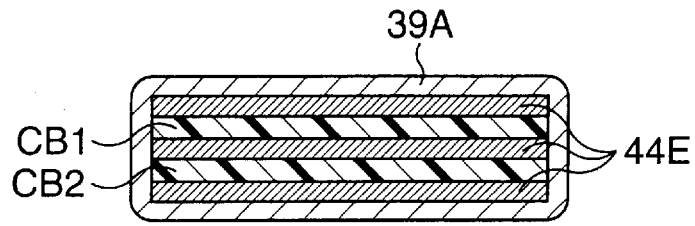
FIGS. 15A to 15D are section views of flexible sheets and flexible circuit board strips.
Figure 15B:
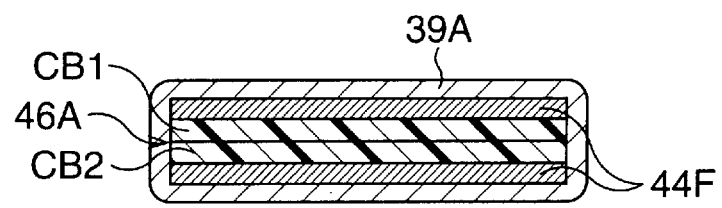
Figure 15C:
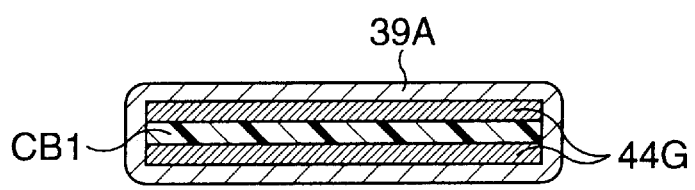
Figure 15D:
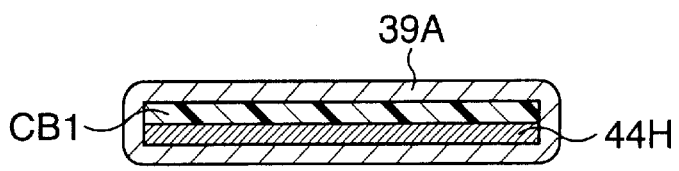

Note that, the flexible sheets and the flexible circuit board strips may be arbitrarily arranged, as shown in FIGS. 15A to 15D. FIG. 15A shows a section view of the flexible circuit board strips CB1 and CB2 and three flexible sheets 44E, which are alternately piled up. FIG. 15B shows a section view of the circuit board bundle 46A and the two flexible sheets 44F, where the circuit board bundle 46A is put between the two flexible sheets 44F. FIG. 15C shows a section view of the flexible circuit board strip CB1 and the two flexible sheets 44G, where the flexible circuit board strip CB1 is put between the two flexible sheets 46G. FIG. 15D shows a section view of the flexible circuit board strip CB1 and the flexible sheet 44H.

Further, the flexible sheets and the flexible circuit board strips may be piled up by using a bonding agent in place of the heat shrinking tubes.

Figure 16:
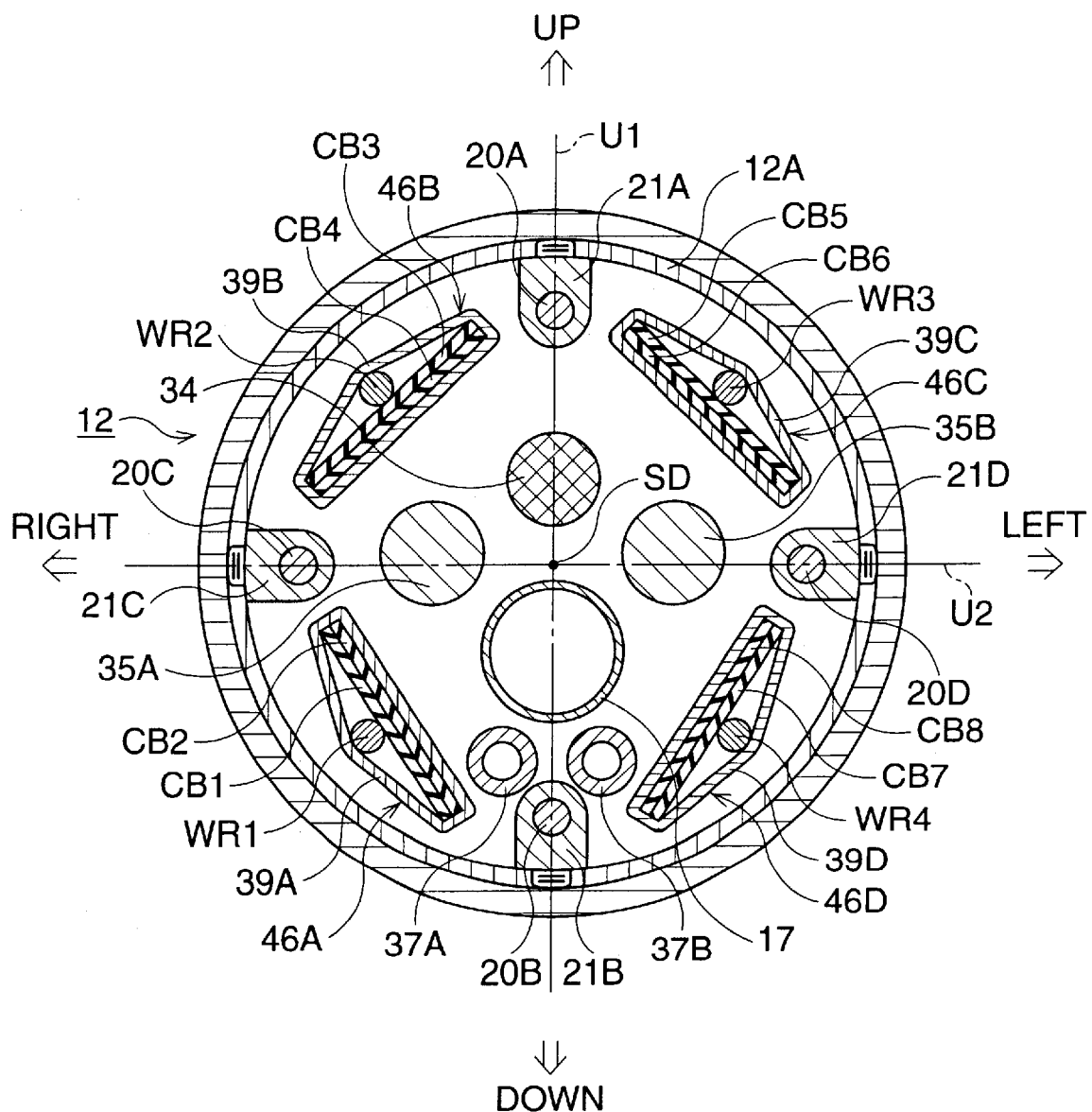
FIG. 16 is a section view of a bending portion of a fourth embodiment.

FIG. 16 shows a section view of a bending portion of a fourth embodiment. The fourth embodiment is different from the first embodiment in that elastic wires are provided.

Elastic wires WR1 to WR4 extend along the central axis SD of the bending portion 12, and extend by a given length corresponding to the longitudinal length of the flexible circuit board strips CB1 to CB8. The elastic wires WR1, WR2, WR3, and WR4 are provided for the circuit board bundles 46A, 46B, 46C, and 46D respectively, and touch the flexible circuit board strips CB1, CB3, CB5, and CB7 respectively.

The elastic wire WR1 touches the flexible circuit board strip CB3 such that the circuit board bundle 46A is put between the elastic wire WR1 and the central axis SD. Similarly, the elastic wires WR2, WR3, and WR4 touch the flexible circuit board strips CB1, CB3, CB5, and CB7, respectively. At this time, the elastic wires WR1, WR2, WR3, and WR4 contact the back surfaces of the flexible circuit board strips CB1, CB3, CB5, and CB7, on which printed wiring is not formed. The elastic wire WR1 and the circuit board bundles 46A are tightly coated by the heat shrinking tube 39A such that the elastic wire WR1 is arranged at the center position along the width "LK2" of the flexible circuit board strips CB1 and CB2. Similarly, the elastic wires WR2, WR3, and WR4 are tightly coated by the heat shrinking tubes 39B, 39C, and 39D, respectively. Each of the elastic wires WR1 to WR4 is composed of metal twist wires using stainless steel, a single metal wire having elastic characteristics, or super-elasticity alloy steel, such as a Ni—Ti (Nickel-Titanium) alloy steel.

In this way, in the fourth embodiment, the elastic wires WR1, WR2, WR3, and WR4 are provided. When the compressing and extending forces operate, the flexible circuit board strips CB1 to CB8 bend smoothly by using the elastic wires WR1 to WR4. As the elastic wires WR1 bends smoothly along an arbitrary direction, the flexible circuit board strips CB1 to CB8 bend smoothly for any direction. Then, as the elastic wires WR1 to WR4 are arranged more adjacent to the ring-shaped segments 12A, the flexible circuit board strips CB1 to CB8 are not caught, or griped by the ring-shaped segments 12A while moving the bending portion 12.

Note that, a wire may be put on an independent flexible circuit board strip, which is shown in FIG. 13, and covered with the heating shrinking tube. Further, the wire and the circuit board bundle may be covered with a silicon tube, which is shown in FIG. 14, before covering with the heat shrinking tube. Elastic wires may be directly bonded to the flexible circuit board strips in place of the heat shrinking tubes.

Figure 17:
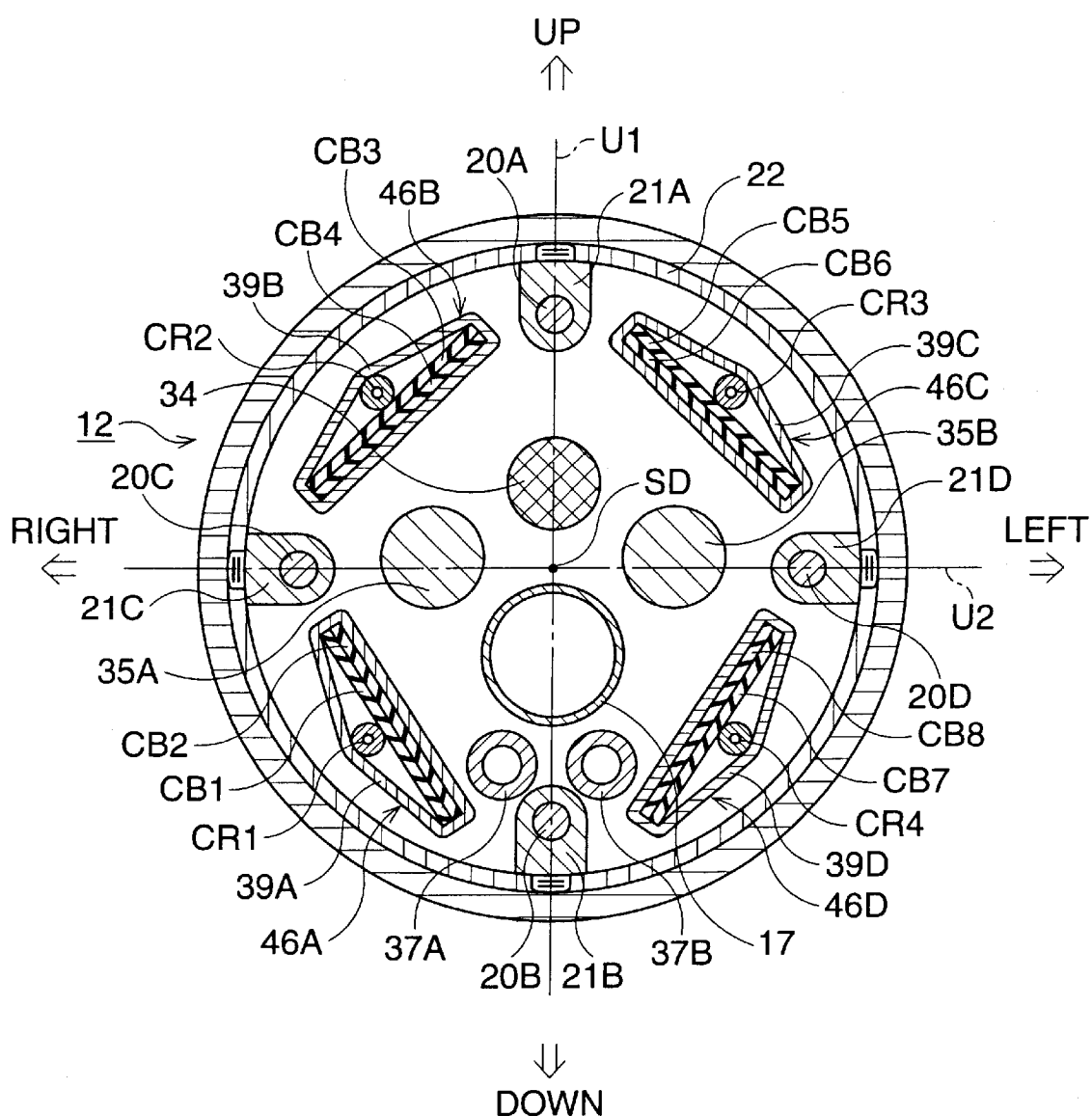
FIG. 17 is a section view of a bending portion of a fourth embodiment.

FIG. 17 shows a section view of a bending portion of a fifth embodiment. The fifth embodiment is different from the fourth embodiment in that a coil spring is provided in place of the elastic wire.

Coil springs CR1 to CR4 extend along the central axis SD of the bending portion 12, and extend by a given length corresponding to the longitudinal length of the flexible circuit board strips CB1 to CB8. The coil springs CR1, CR2, CR3, and CR4 are provided for the circuit board bundles 46A, 46B, 46C, and 46D respectively, and touch the flexible circuit board strips CB1, CB3, CB5, and CB7 respectively.

The coil spring CR1 touches the flexible circuit board strip CB3 such that the circuit board bundle 46A is put between the elastic wire WR1 and the central axis SD. Similarly, the coil springs CR2, CR3, and CR4 touch the flexible circuit board strips CB1, CB3, CB5, and CB7, respectively. At this time, the coil springs CR1, CR2, CR3, and CR4 contact the back surfaces of the flexible circuit board strips CB1, CB3, CB5, and CB7, on which printed wiring is not formed. The coil spring CR1 and the circuit board bundles 46A are tightly coated by the heat shrinking tube 39A such that the coil spring CR1 is arranged at the center position along the width "LK2" of the flexible circuit board strips CB1 and CB2. Similarly, the coil springs CR2, CR3, and CR4 are tightly coated by the heat shrinking tubes 39B, 39C, and 39D, respectively.

The coil springs CR1 to CR4 are formed by winding wire, such as stainless steel, into spring. The section of each of the coil springs CR1 to CR4 is circular and in spirals such that the radius of the coil spring is constant. Note that, the section form of the wire may be other shape, such as plate.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 2000-353740 (filed on Nov. 21, 2000), No. 2000-353741 (filed on Nov. 21, 2000), No. 2000-353742 (filed on Nov. 21, 2000), No. 2000-353743 (filed on Nov. 21, 2000), and No. 2000-353744 (filed on Nov. 21, 2000) which are expressly incorporated herein, by reference, in their entireties.

What is claimed is:

1. An ultrasonic endoscope comprising:
    a bending portion in a tube and connected to a flexible tube insertable into a body, said bending portion being bent along two predetermined bending-directions perpendicular to each other, by remote control;
    an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves;
    a flexible circuit board that transmits signals associated with the ultrasonic waves and the echoes, said flexible circuit board comprising a plurality of flexible circuit board strips in said bending portion so as to allow a bending motion, said plurality of flexible circuit board strips extending along a central axis of said bending portion, wherein said plurality of flexible circuit board strips are durable for the bending motion of said bending portion;
    a plurality of elastic members that extend along the central axis, each of said plurality of elastic members touching a corresponding flexible circuit board strip among said plurality of flexible circuit board strips; and
    heat shrinking tubes that coat said plurality of elastic members and said plurality of flexible circuit board strips after a heat shrinking process.

2. The ultrasonic endoscope of claim 1, wherein each of said elastic members touches the corresponding flexible circuit board strip such that the corresponding flexible circuit board strip is between a contacting elastic member and the central axis in a section of said bending portion.

3. An ultrasonic endoscope comprising:
    a bending portion in a tube and connected to a flexible tube insertable into a body, said bending portion being bent along two predetermined bending-directions perpendicular to each other, by remote control;
    an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves;
    a flexible circuit board that transmits signals associated with the ultrasonic waves and the echoes, said flexible circuit board comprising a plurality of flexible circuit board strips in said bending portion so as to allow a bending motion, said plurality of flexible circuit board strips extending along a central axis of said bending portion, wherein said plurality of flexible circuit board strips is durable for the bending motion of said bending portion; and
    a plurality of elastic members that extend along the central axis, each of said plurality of elastic members comprising an elastic wire and touching a corresponding flexible circuit board strip among said plurality of flexible circuit board strips.

4. The ultrasonic endoscope of claim 3, wherein each of said elastic members is comprised of one of, metal twist wires, a single metal wire having elastic characteristics, and super-elasticity alloy steel.

5. An ultrasonic endoscope comprising:
    a bending portion in a tube and connected to a flexible tube insertable into a body, said bending portion being bent along two predetermined bending-directions perpendicular to each other, by remote control;
    an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves;
    a flexible circuit board that transmits signals associated with the ultrasonic waves and the echoes, said flexible circuit board comprising a plurality of flexible circuit board strips in said bending portion so as to allow a bending motion, said plurality of flexible circuit board strips extending along a central axis of said bending portion, wherein said plurality of flexible circuit board strips is durable for the bending motion of said bending portion; and
    a plurality of elastic members that extend along the central axis, each of said plurality of elastic members comprising a coil spring and touching a corresponding flexible circuit board strip among said plurality of flexible circuit board strips.

6. An ultrasonic endoscope comprising:
    a bending portion in a tube and connected to a flexible tube insertable into a body, said bending portion being bent along two predetermined bending-directions perpendicular to each other, by remote control;
    an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves;

a flexible circuit board that transmits signals associated with the ultrasonic waves and the echoes, said flexible circuit board comprising a plurality of flexible circuit board strips in said bending portion so as to allow a bending motion, said plurality of flexible circuit board strips extending along a central axis of said bending portion, wherein said plurality of flexible circuit board strips is durable for the bending motion of said bending portion;

a plurality of flexible sheets that extend along the central axis, each of said plurality of flexible sheets being piled on a corresponding flexible circuit board strip among said plurality of flexible circuit board strips; and heat shrink tubes that extend along the central axis and coat said plurality of flexible circuit board strips and said plurality of flexible sheets after a heat shrinking process.

7. An ultrasonic endoscope comprising:

a bending portion in a tube and connected to a flexible tube insertable into a body, said bending portion being bent along two predetermined bending-directions perpendicular to each other, by remote control;

an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves;

a flexible circuit board that transmits signals associated with the ultrasonic waves and the echoes, said flexible circuit board comprising a plurality of flexible circuit board strips in said bending portion so as to allow a bending motion, said plurality of flexible circuit board strips extending along a central axis of said bending portion, wherein said plurality of flexible circuit board strips is durable for the bending motion of said bending portion; and flexible protecting members that extend along the longitudinal direction of the flexible circuit board strips and cover the totality of the flexible circuit board strips.

8. The ultrasonic endoscope of claim 7, wherein said flexible protecting members are heat shrinking tubes that coat said plurality of flexible circuit board strips after a heat shrinking process.

9. The ultrasonic endoscope of claim 7, wherein a plurality of bundles, each of which is composed of at least two flexible circuit board strips, is formed for said plurality of flexible circuit board strips, and wherein each bundle in said plurality of bundles is coated by a corresponding flexible protecting member.

10. An ultrasonic endoscope comprising:

a bending portion in a tube and connected to a flexible tube insertable into a body, said bending portion being bent along two predetermined bending-directions perpendicular to each other, by remote control;

an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves;

a flexible circuit board that transmits signals associated with the ultrasonic waves and the echoes, said flexible circuit board comprising:

a plurality of flexible circuit board strips in said bending portion so as to allow a bending motion, said plurality of flexible circuit board strips extending along a central axis of said bending portion, wherein said plurality of flexible circuit board strips is durable for the bending motion of said bending portion which is connected to said ultrasonic probe, a first printed wiring on said plurality of flexible circuit board strips is bolder than a second printed wiring on a connecting portion of said flexible circuit board that is connected to said ultrasonic probe, a width of the connecting portion corresponding to a scanning range, the combined width of each of the plurality of circuit board strips is larger than the width of the connecting portion to make the first printed wiring bolder than the second printed wiring, and the first printed wiring has sufficient boldness to prevent the first printed wiring from snapping during the bending motion; and said flexible circuit board comprising a single rectangular flexible circuit board having an arcuate shape, said plurality of flexible circuit board strips being defined by slits in said rectangular flexible circuit board, wherein a length of each of the plurality of circuit board strips of the rectangular flexible circuit board is longer than a length of said connecting portion.

* * * * *